(12) United States Patent
Franklin

(10) Patent No.: US 12,744,119 B2
(45) Date of Patent: Sep. 22, 2026

(54) CAPITAL EQUIPMENT AUTO-ENABLED FEATURES

(71) Applicant: C. R. Bard, Inc., Franklin Lakes, NJ (US)

(72) Inventor: Jeff E. Franklin, Hamilton, OH (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 206 days.

(21) Appl. No.: 18/276,855

(22) PCT Filed: Feb. 9, 2022

(86) PCT No.: PCT/US2022/015846

§ 371 (c)(1),
(2) Date: Aug. 10, 2023

(87) PCT Pub. No.: WO2022/177791

PCT Pub. Date: Aug. 25, 2022

(65) Prior Publication Data

US 2024/0120083 A1 Apr. 11, 2024

Related U.S. Application Data

(60) Provisional application No. 63/150,435, filed on Feb. 17, 2021.

(51) Int. Cl.
*G16H 40/40* (2018.01)

(52) U.S. Cl.
CPC .................................. *G16H 40/40* (2018.01)

(58) Field of Classification Search
CPC ........ G16H 40/40; G16H 20/40; G16H 40/20; G16H 40/63
See application file for complete search history.

(56) References Cited

U.S. PATENT DOCUMENTS 5,897,142 A 4/1999 Kulevsky
7,434,842 B2 10/2008 Schmidt
(Continued)

FOREIGN PATENT DOCUMENTS

EP 1110504 A2 6/2001
EP 3506311 A1 * 7/2019 ............ A61B 18/14
(Continued)

OTHER PUBLICATIONS

Junnila, Sakari. “Modern Digital Interfaces for Personal Health Monitoring Devices.” G5 Doctoral dissertation. Tampere University of Technology. vol. 858: 1459-2045. (Year: 2009).*
(Continued)

*Primary Examiner* — Linh Giang Le
(74) *Attorney, Agent, or Firm* — Rutan & Tucker LLP

(57) ABSTRACT

Disclosed herein is a medical system including an equipment module, a limited use device, and a functional interface configured to operatively couple the limited use device with the equipment module via a non-proprietary connector. The equipment module includes an identification interface configured to obtain identification data from the limited use device, and the equipment module is configured to modify operation of the system in accordance with a result of obtaining the identification data. A method of operation includes disabling operating features if the brand of the limited use device is different from the brand of the equipment module. Computer logic and a computerized method include detecting coupling of an equipment module to a console and attempting to obtain identification data of the equipment module. As a result, the console enables either a first set or a second set of operations.

20 Claims, 3 Drawing Sheets

(56) References Cited

U.S. PATENT DOCUMENTS

| | | | |
|---|---|---|---|
| 8,683,996 | B2 | 4/2014 | Allen et al. |
| 9,283,109 | B2 | 3/2016 | Guyuron et al. |
| 9,750,873 | B2 * | 9/2017 | Brown ............... H01R 13/5224 |
| 2009/0306634 | A1 * | 12/2009 | Caiado de Castro Neto ............... A61F 9/008 606/4 |
| 2013/0138185 | A1 | 5/2013 | Paxman et al. |
| 2014/0046411 | A1 | 2/2014 | Elkins et al. |
| 2018/0042762 | A1 | 2/2018 | Galer |
| 2018/0163907 | A1 | 6/2018 | Brugger et al. |
| 2019/0192337 | A1 | 6/2019 | Taylor et al. |
| 2020/0289361 | A1 | 9/2020 | Tian et al. |

FOREIGN PATENT DOCUMENTS

| | | | |
|---|---|---|---|
| WO | 03094090 | A2 | 11/2003 |
| WO | 2022177791 | A1 | 8/2022 |

OTHER PUBLICATIONS

PCT/US2022/015846 filed Feb. 9, 2022 International Search Report and Written Opinion dated Apr. 26, 2022.

* cited by examiner

CAPITAL EQUIPMENT AUTO-ENABLED FEATURES

PRIORITY

This application is a U.S. national stage application of International Application No. PCT/US2022/015846, filed Feb. 9, 2022, which claims the benefit of priority to U.S. Provisional Application No. 63/150,435, filed Feb. 17, 2021, each of which is incorporated by reference in its entirety into this application.

BACKGROUND

The medical treatment of patients often includes the use of a system comprising a piece of capital equipment and a limited use device such as a consumable device or a single use device. The capital equipment may be configured for numerous operations over several years, while the limited use device may be rendered unusable after just a few operations. In some cases, the limited use devices may degrade with use requiring replacement at regular intervals. In some instances, a sterile limited use device may become contaminated during use preventing subsequent use.

In some instances, the limited use device may be validated to be suitable for use over a short period such as single day or a single treatment, for example. In some instances, a user may attempt to use the limited use device beyond the validated period of use. Use of limited use devices beyond the validated period of use may put a patient's health at risk as well as increase the liability of the care provider.

Similar to the period of use validation, the capital equipment and the limited use device may be validated together as a system. As such, the manufacturer's safety assurance may be valid only if the capital equipment is used with the limited use device that was validated as part of the system. It is common for a third party to manufacture limited use devises to be used with capital equipment. As such, any testing performed for the third-party limited use device may be less than the validation testing performed for the original limited use device resulting in a potential risk to the patient's health. Furthermore, the original manufacturer may make periodic improvements to the original limited use device that may not be incorporated into the third-party device.

To discourage or inhibit use of third-party limited use devices, medical device manufactures have historically attempted to incorporate proprietary connection systems between the capital equipment and the limited use device. However, some countries have enacted policies to prevent the locking out of third-party limited use providers via proprietary connection systems. Furthermore, in order to better provide for affordable medical care, it may be advantageous for medical device manufacturers to incorporate standard connection systems, i.e., connectors that comply with established industry standards.

In summary, there is a need to encourage health care providers to minimize the patient risk and the liability risk associated with the use of third-party limited use devices. Disclosed herein are systems and methods for encouraging health care providers to use original equipment limited use devices together with their associated capital equipment.

SUMMARY OF THE INVENTION

Briefly summarized, disclosed herein is a medical system comprising an equipment module, a limited use device, and a functional interface configured to operatively couple the limited use device with the equipment module. The equipment module includes an identification interface configured to obtain identification data from the limited use device, and the equipment module is configured to modify operation of the system in accordance with a result of obtaining the identification data.

The medical system may be configured to provide a medical treatment to a patient. The limited use device may be configured to operatively engage the patient and/or contact the patient. The functional interface may be at least partially defined by one or more industry standards and the functional interface may be non-proprietary.

The identification interface may be coupled to a console of the equipment module and the console may include a processor and memory including identification logic stored thereon. The identification logic may be configured so that, when executed by the processor, identification logic may modify the operation of the system in accordance with the result of obtaining the identification data. The identification logic may be configured to modify one or more treatment parameters of the system in accordance with the result of obtaining the identification data, and the identification logic may be configured to selectively enable and/or disable one or more operating features of the medical system in accordance with the result of obtaining the identification data.

The identification interface may be configured to wirelessly receive an identity signal from the limited use device and the identity signal may include the identification data.

The identification data may include a set of identification parameters, and the memory may include a corresponding set of identification parameters. An operation of the identification logic may include comparing an identification parameter of the identification data with a corresponding identification parameter stored in memory, and the identification logic is configured to modify the operation of the system in accordance with a result of the comparison.

The identification logic my further be configured to disable one or more operating features if the result of the comparison indicates that at least one identification parameter in the identification data is inconsistent with the corresponding identification parameter stored in memory. The identification logic may also be configured to allow operation of the medical system according to a minimal set of operating features if the result of the comparison indicates that the at least one identification parameter is inconsistent with the corresponding identification parameter. In some embodiments, the set of identification parameters includes at least a brand of the limited use device.

Also, disclosed herein is a method of operating a medical system. The method includes providing a medical system including a console having software stored thereon, where the console has a connector port configured for coupling with an equipment module connector, and wherein the software (i) attempts to obtain identification information of the equipment module, (ii) enables a first set of operations when the equipment module is identifiable, and (iii) enables a second set of operations when the equipment module is unidentifiable. The method further includes operatively coupling the equipment module to the console via a non-proprietary connector, attempting to obtain identification information from the equipment module, determining that the equipment module is unidentifiable, enabling the second set of operations in accordance with a result of determining that the equipment module is unidentifiable, and utilizing the second set of operations while operating the medical system.

The method may further include providing a medical treatment to a patient while operating the medical system. In some embodiments, the equipment module is configured to operatively engage the patient.

The method may further include wirelessly receiving an identity signal from the equipment module, the identity signal including the identification information.

In some embodiments, the equipment module includes a cable coupled to the console via the non-proprietary connector and the cable maybe a fiber-optic cable.

The medical system may include a laser generator, and the medical treatment include a laser-based treatment.

Also disclosed herein is a non-transitory, computer-readable medium having stored thereon logic, that when executed by one or more processors, causes performance of operations that include detecting coupling of an equipment module to a console and attempting to obtain identification data of the equipment module. When the identification data is obtained and the equipment module is identified, the operations include enabling the console to provide a first set of operations based on the identification data; and when the identification data is unable to be obtained, the operations include enabling the console to provide a second set of operations. The second set of operations may be a subset of the first set of operations.

In some embodiments of the non-transitory, computer-readable medium, the console is included in a medical system configured to provide a therapy to a patient, the equipment module is a medical device, and the second set of operations includes a minimal set of operations for using the medical system to provide the therapy via the medical device.

In some embodiments of the non-transitory, computer-readable medium, the first set of operations includes a first therapy range, the second set of operations includes a second therapy range, and the second therapy range is less than the first therapy range.

In some embodiments of the non-transitory, computer-readable medium, the medical system includes a laser for performing a laser therapy, the first set of operations includes a first operating range of the laser, the second set of operations includes a second operating range of the laser, and the second operating range is less than the first operating range.

In some embodiments of the non-transitory, computer-readable medium, the medical system includes one or more optional operations, the first set of operations includes at least one optional operation, and the second set of operations does not include at least one optional operation of the first set.

Also disclosed herein is a computerized method which includes detecting coupling of an equipment module to a console and attempting to obtain identification data of the equipment module. When the identification data is obtained and the equipment module is identified, the method further includes enabling the console to provide a first set of operations based on the identification data, and when the identification data is unable to be obtained, the method further includes enabling the console to provide a second set of operations.

In some embodiments of the computerized method, the second set of operations is a limited set of operations and in some embodiments, the second set of operations is a subset of the first set of operations.

In some embodiments of the computerized method, the console is included in a medical system configured to provide a therapy to a patient, the equipment module is a medical device, and the second set of operations includes a minimal set of operations for using the medical system to provide the therapy via the medical device.

In some embodiments of the computerized method, the first set of operations includes a first therapy range, the second set of operations includes a second therapy range, and the second therapy range is less than the first therapy range.

In some embodiments of the computerized method, the medical system includes a laser for performing a laser therapy, the first set of operations includes a first operating range of the laser, the second set of operations includes a second operating range of the laser, and the second operating range is less than the first operating range.

In some embodiments of the computerized method, the medical system includes one or more optional operations, the first set of operations includes at least one optional operation, and the second set of operations does not include at least one optional operation of the first set.

These and other features of the concepts provided herein will become more apparent to those of skill in the art in view of the accompanying drawings and the following description, which describe particular embodiments of such concepts in greater detail.

BRIEF DESCRIPTION OF DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which.

DETAILED DESCRIPTION

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise. The words "including," "has," and "having," as used herein, including the claims, shall have the same meaning as the word "comprising." Furthermore, the terms "or" and "and/or" as used herein are to be interpreted as inclusive or meaning any one or any combination. As an example, "A, B or C" or "A, B and/or C" mean "any of the following: A; B; C; A and B; A and C; B and C; A, B and C." An exception to this definition will occur only when a combination of elements, components, functions, steps or acts are in some way inherently mutually exclusive.

The phrases "connected to" and "coupled to" refer to any form of interaction between two or more entities, including mechanical, electrical, magnetic, electromagnetic, fluid, signal, communicative (including wireless), and thermal interaction. Two components may be connected or coupled to each other even though they are not in direct contact with each other. For example, two components may be coupled to each other through an intermediate component. Unless defined otherwise, all technical and scientific terms used herein have the same meaning as commonly understood by those of ordinary skill in the art.

Figure 1:
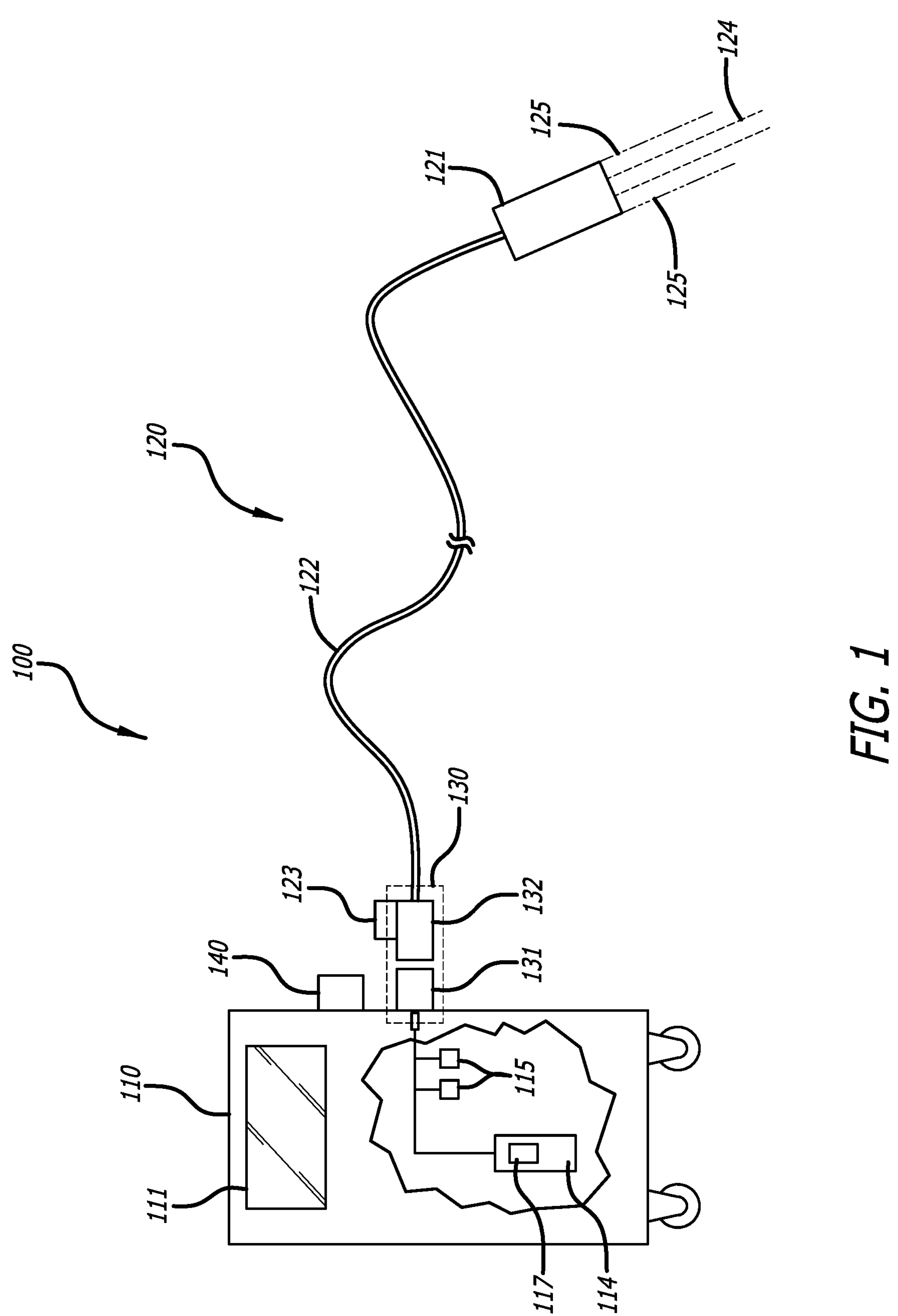
FIG. 1 is an illustration of a medical system including an equipment module and a limited use device, in accordance with some embodiments.

FIG. 1 illustrates a medical system 100 including an equipment module 110 coupled to a limited use device 120. In some embodiments, the limited use device 120 may be configured for a limited number of uses such as a single use or for use on a single patient. In other embodiments, the limited use device 120 may not be configured for a limited number of uses. In other words, the limited use device 120 may be an equipment module configured for an unlimited number of uses. The system 100 may be configured to facilitate at least a portion of a treatment to a patient. The treatment may include any physical interaction with the patient. By way of example, the treatment may include the application of a therapy to the patient or the treatment may include the assessment of a condition of the patient. In other examples, the treatment may include the preparation of a fluid to be administered to the patient in accordance with a prescribed or potential therapy. Other forms of patient treatment, as may be contemplated one of ordinary skill, are also included herein. The system 100 may include multiple modes of operation. Each mode of operation may include multiple operating features of which one or more may be optional features. Some operating features may include operating parameters of the system that may be specific to the treatment. In some embodiments, the operating features may include features that facilitate the performance of logistical activities associated with patient care generally such as the recording a patient data, for example.

The operating features may include features related to a connection to a facility network. Such features may include displaying data from the system 100 on a remote monitor, printing a treatment report, and saving treatment data to a patient profile such as a profile associated with an electronic medical record (EMR) for the patient.

In some embodiments, the operating features may be associated with the limited use device 120. In some embodiments, the system 100 may be configured to operate in accordance with multiple models or versions of the limited use device 120. The multiple models may be configured to accommodate multiple types of patients and/or facilitate multiple types of treatments. As such, some operating features may be configured to facilitate operation of system 100 in accordance with a specific model of the limited use device 120.

In some embodiments, the limited use device 120 may include a patient engagement device 121 and a cable 122 extending between the equipment module 110 and the patient engagement device 121. The patient engagement device 121 may operatively engage the patient which may include directly contacting the patient. The multiple models of the limited use device 120 may be at least partially defined by different characteristics of the patient engagement device 121. The different characteristics may be configured to facilitate different treatments. The operating features may include features configured to facilitate operation of system 100 in accordance with specific characteristics of the patient engagement device 121.

In other embodiments, the operating features may be associated with the treatment. By way of example, the operating features may be configured to adjust operating parameters of the system 100 according to patient parameters such as size and/or weight. In some embodiments, the treatment may be performed with a patient engagement device 121 configured to accommodate a patient size. For example, a first model (e.g., "large") of the patient engagement device 121 may be used to treat an adult patient and a second model (e.g., "small") of the patient engagement device 121 may be used to treat a pediatric patient. In similar fashion, one set of operating features may be used in conjunction with the first model of the patient engagement device 121 and another set of operating features may be used in conjunction with the second model of the patient engagement device 121.

The operation of the system 100 may include the transfer of energy to or from the patient. The operation may include the transmission of energy between the equipment module 110 and the patient engagement device 121 along the cable 122. In some embodiments, the energy may be in the form of mechanical energy such the rotation of a shaft or the longitudinal displacement of the shaft. In further embodiments, the energy may be a fluid energy in the form of pressure and/or flow of a fluid. In further embodiments, the energy may be electrical. Still in further embodiments, the energy may be in the form of light such as energy from a laser. In some embodiments, the treatment may include the transmission of the energy in multiple forms such as any combination of the mechanical, fluid, electrical, and light energies described above. In some embodiments, the level of energy may be low such as a level of energy suitable for data transmission or signal transmission, such as from a sensor. In other embodiments, the level of energy may be elevated to a level sufficient to apply energy to the patient such as heat, electrical shock, a mechanical force/displacement, and/or fluid to a patient in accordance with the treatment. In summary, the treatment may include the exchange of any form of energy at any level between the equipment module 110 and the patient. Similarly, the operation of the system 100 may include the exchange of any form of energy at any level between the equipment module 110 and the limited use device 120.

The patient engagement device 121 may be any device suitable for the application of the treatment to the patient. The patient engagement device 121 may be a passive device (i.e., having no energy source) or the patient engagement device 121 may include an energy source such as a battery. The patient engagement device 121 may be defined for limited use, such as for a one-time application of a treatment.

In other embodiments, the patient engagement device 121 may be defined for use on a single patient.

The patient engagement device 121 is operatively coupled to the cable 122 to facilitate transfer of energy between the patient engagement device 121 and the cable 122. The patient engagement device 121 may also be physically attached to the cable 122. The attachment of the patient engagement device 121 to the cable 122 may be configured to prevent or inhibit detachment. In other embodiments, the patient engagement device 121 may be detachable from the cable 122.

The cable 122 may be configured for unidirectional or bidirectional transfer of energy. As such, the cable 122 may include one or multiple energy transfer elements (not shown). The energy transfer elements may include fluid lumens, electrical conductors, mechanical cables, fiber-optic filaments, or any combination thereof. In some embodiments, two or more energy transfer elements may be arranged coaxially.

The cable 122 is coupled to the equipment module 110 via a functional interface 130. The functional interface 130 may allow for selective coupling and decoupling of the cable 122 to and from the equipment module 110. The cable 122 is operatively coupled to the equipment module 110 to facilitate transfer of the energy between the equipment module 110 and the cable 122. In other words, the functional interface 130 provides for operative coupling between the patient engagement device 121 and the equipment module 110. As such, in use, the energy passes through functional interface 130.

The functional interface 130 may include a connector set that at least partially complies with an industry standard. The connector set includes an equipment connector 131 attached to the equipment module 110 and a complimentary cable connector 132 attached to the cable 122. The equipment connector 131 may sufficiently comply with an industry connector standard so that the cable connector 132 may be commercially available as an off-the-shelf connector. As such, the equipment connector 131 may not require the cable connector 132 to include unique or proprietary specifications or features. In other words, the equipment connector 131 may be capable of coupling with a commercially-available off-the-shelf connector. Use of connectors that comply with an industry standard and that are commercially available may help minimize the cost of the equipment module 110 and the patient engagement device 121 which may also minimize the cost of providing health care. In some embodiments, the equipment connector 131 may include specifications consistent with commercially-available sub-miniature version A (SMA) connectors such as SMA-905 connectors.

The cable connector 132 may include additional features that provide for increased functionality of the cable connector 132. For example, the cable connector 132 may be configured to enhance the reliability of the limited use device 120 and/or the ease-of-use for the clinician. The cable connector 132 may further be configured to enhance the manufacturability of the limited use device 120 including the cable 122. For example, the cable connector 132 may be configured to facilitate injection molding, automated assembly, or any other suitable manufacturing process of the limited use device 120.

The system 100 further includes an identification interface 140 operatively coupled to the equipment module 110. The identification interface 140 may be configured to obtain an identity of the limited use device 120. The limited use device 120 may be configured to provide identification data 123 (sometimes referred to herein as identification information) to the identification interface 140. In use, the identification interface 140 may read, or otherwise learn, the identity of the limited use device 120.

The limited use device 120 may include machine-readable identification data 123 that contains identifying information related to the limited use device 120. The identifying information may include a manufacturer's brand, a model designation, a date of manufacture, a serial/lot number, or any other suitably identifying information or data. In some embodiments, the identifying information may uniquely identify the limited use device 120, such that no two patient engagement device units include the same identification data 123.

In some embodiments, the identification data 123 may be disposed on an outside surface of the limited use device 120. The identification data 123 may be printed on the limited use device 120 in the form of a machine-readable code such as a barcode or matrix code. In some embodiments, the identification data 123 may be human readable as well. In some embodiments, the identification data 123 may be included in an electronic data packet, such as a data packet associated with a radio frequency identification (RFID) chip of the patient engagement device 121.

The identification interface 140 may be configured to read (or otherwise obtain) the identification data 123 and thus determine the identity of the limited use device 120. In some embodiments, the identification interface 140 may include an imaging device capable of reading identification data 123 that is printed such as a barcode or matrix code. In some embodiments, the imaging device be configured to read identification data 123 that is human readable via optical character recognition (OCR) capability.

In some embodiments, the identification interface 140 may include an RFID chip reader. In such embodiments, the limited use device 120 may be configured such that the identification data 123 is obtainable by the identification interface 140 when the limited use device 120 is coupled to, or in close proximity to, the equipment module 110. In some embodiments, the identification interface 140 may be configured such that the identification data 123 is obtainable by the identification interface 140 when the equipment connector 131 is coupled to the cable connector 132.

The equipment module 110 may include various internal active and passive components to facilitate operation of the system 100 and provide the treatment to the patient. The equipment module 110 may include an energy source 114. The energy source 114 is coupled to the equipment connector 131 so that sourced energy may be transferred to the limited use device 120. The equipment module 110 may also include a graphical user interface (GUI) 111 through which the clinician may interact with the system 100.

In some embodiments, the system 100 may include a remote controller 112. The remote controller 112 may be coupled to the equipment module 110 via a wired or wireless connection. The remote controller 112 may be configured to allow the clinician to at least partially operate system 100 from a location spaced away from the equipment module 110. In some instances, it may be advantageous to locate the remote controller 112 at the patient so that the system 100 may be operated by the clinician while engaging the patient. The remote controller 112, may also include a display 113 for rendering information related to operation of the system 100 and/or treatment of the patient. In some embodiments, the remote controller 112 may be configurable by a console of the system 100 as further described below.

In some embodiments, the system 100 may include a pedal controller 116. The pedal controller 116 may be coupled to the equipment module 110 via a wired or wireless connection. The pedal controller 116 may be configured to allow the clinician to at least partially operate system 100 with a foot. In some embodiments, the clinician, via the pedal controller 116, may turn the energy source 114 on/off and/or adjust an energy level of the energy source 114. In some embodiments, the foot controller 116 may also be configurable by a console of the system 100.

In an embodiment, the system 100 may be configured to perform a laser treatment such as an endourological treatment. In such an embodiment, the energy device 114 may include a laser generator 117 operatively coupled to the equipment connector 131. The cable 122 may include a fiber optic cable and the patient engagement device 121 may be configured to deliver a laser beam 124 to the patient to perform the laser treatment. The laser generator 117 may be configured to operate at multiple pulse energy levels and pulse frequency levels.

The system 100 may also include one or more additional light sources 115 within the equipment module 110. The light sources 115 may include light emitting diodes (LEDs) of multiple colors. The light sources 115 may be operatively coupled to the patient engagement device 121 via the cable 122 such that multi-colored aiming beams 125 may be emitted from the patient engagement device 121. As the laser beam 124 may be non-visible, the aiming beams 125 may indicate the position of the laser beam 124 on the patient. In some embodiments, the patient engagement device 121 may or may not be compatible with aiming beams 125 in accordance with a model designation.

Figure 2:
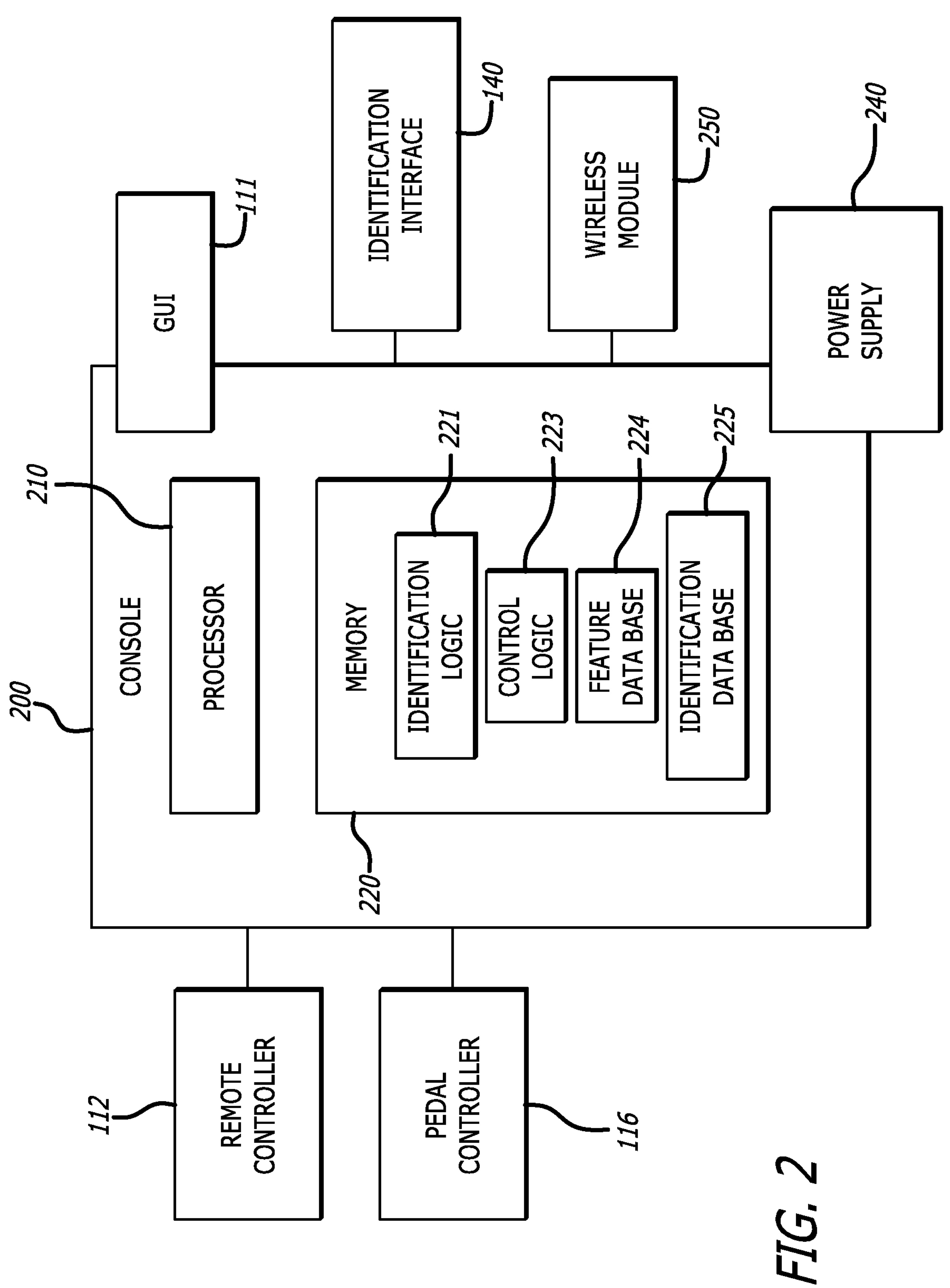
FIG. 2 illustrates a block diagram of the medical system depicting various elements of a console of the equipment module of FIG. 1, in accordance with some embodiments.

FIG. 2 illustrates a block diagram depicting various elements of the equipment module 110 of FIG. 1, in accordance with some embodiments. The equipment module 110 includes a console 200 including a processor 210 and memory 220 which may be a non-transitory, computer-readable storage medium. Stored in the memory 220 are logic modules including at least identification logic 221 and system control logic 223. The memory further includes an identification parameter data base 225 and a feature data base 224. As stated above, the remote controller 112, the foot controller 116, and the identification interface 140 are each coupled to the console 200. The console 200 further includes, or is coupled to, the graphical user interface (GUI) 111 and the console 200 receives electrical power from a power supply 240 which may be internal or external to the equipment module 110. A wireless module 250 provides for wireless communication to external networks and/or devices.

The GUI 111 is configured to receive input from the clinician. The clinician input data may include treatment parameters, patient parameters, and other parameters related to the care of the patient and/or operation of the system 100. The GUI 111 further displays system information related to the operation of the system 100 and the treatment of the patient. The identification interface 140 provides identification data 123 to the console 200 to be processed by the processor 210 in accordance with the identification logic 221 as further described below.

The console 200 includes a feature data base 224 stored in the memory 220. The feature data base 224 may include multiple operating features which may be arranged in feature sets. The feature sets may include a basic operating feature set that includes a minimal set of operating features required for operation of the system 100. The feature sets may further include one or more extended feature sets. The extended feature sets include optional features that may be combined with the basic operating feature set to enhance the operation of the system 100. As such, the system 100 may be operated according to the basic operating feature set alone or according to the basic operating feature set in combination with one or more extended feature sets. The extended feature sets may include features related to health care activities that do not affect the treatment of the patient. The extended feature sets may also include features that affect operating parameters related to the treatment. In some embodiments, the extended feature sets may include operating features that modify a range of operating parameters of the system 100. In some embodiments, the operating features may include:

a) automatic recording of treatment parameters;
b) automatic input of patient parameters such as age, size, weight, etc., via connection to a facility network
c) displaying of system data on a remote monitor;
d) interacting with an EMR system;
e) using a remote controller of the system;
f) automatic recording of identification data of limited use devices 120 coupled to the equipment module 110;
g) automatic setting of laser operating parameters in accordance with identification data of the connected limited use device 120;
h) adjusting a range of laser pulse energy levels that may exceed the basic range of laser pulse energy levels;
i) adjusting a range of laser pulse frequency levels that may exceed the basic range of laser pulse frequency levels; and/or
j) automatic setting of laser operating parameters in accordance with patient parameters.

As may be appreciated by one of ordinary skill, the list of features for a medical system may be include an many more features pertaining to the medical system 100 or use of the medical system 100 within a health care provider's environment. The number of features may also increase over the lifetime of the system 100. As such, the extended feature set as defined herein may include any features that may be combined with a minimal set of operating features required for operation of the system 100. In some embodiments, the feature data base 224 may be modified throughout the life of the system 100 to include additional operating features or delete existing operating features. In some embodiments, the system 100 may be connected to a network which may facilitate automatic modification of the feature data base 224.

The identification data base 225 includes stored identification parameters associated with the patient engagement device 121. The stored identification parameters may include the manufacturer's brand, the model identification, a date range of manufacture, a serial number range, or any other suitably identifying parameters for the patient engagement device 121. In use, one or more of the stored identification parameters may be compared with identification data 123 acquired by identification interface 140. In some embodiments, the stored identification parameters may be updated throughout a lifetime of the system 100.

The identification logic 221 is configured to compare the identification data 123, as obtained by identification interface 140, with identification parameters of the identification database 225. As a result of the comparison, identification logic 221 may enable or disable (i.e., allow or disallow the use of) one or more extended feature sets. In use, the clinician connects a limited use device 120 with the equipment module 110 and the identification interface 140 obtains the identification data 123 from the limited use device 120. The identification logic 221 then compares the identification data 123 with the identification parameters stored on the identification data base 225. The identification logic 221 then enables or disables one or more operating features in response to the comparison.

By way of example, in one instance, the clinician may connect a limited use device 120 obtained from a manufacturer different from the manufacturer of the system 100. In such an instance, the manufacturer's brand obtained by the identification interface 140 may be inconsistent with (i.e., not match) the manufacturer's brand stored in the identification data base 225. As a result, the identification logic 221 may allow the use of only the basic operating feature set. In an alternative instance, the clinician may connect a limited use device 120 obtained from the manufacturer of the system 100. In this alternative instance, the manufacturer's brand, as obtained by the identification interface 140, will be consistent with (i.e., match) the manufacturer's brand in the identification data base 225 and as a result, the identification logic 221 may allow the use of an extended feature set in addition to the basic operating feature set.

By way of another example, in some embodiments, the system 100 may include multiple models or versions of the limited use device 120 which are different from one another and the different models may be configured to utilize different operating features of the system 100. In such embodiments, the identification interface 140 may obtain a model designation of the limited use device 120, and the identification logic 221 may compare the acquired model designation with multiple model designations stored in the identification data base 225. As a result of the comparison, the logic 221 may enable an extended feature set corresponding with the connected model of the limited use device 120.

By way of another example, in some instances, a manufacturing lot of limited use devices 120 may be defective or otherwise deemed inappropriate for use with the system 100. In such an instance, the identification data base 225 may be updated via a network connection to include a manufacturing date range and/or a lot number range associated with the defective manufacturing lot. In use, the identification interface 140 may obtain the manufacturing date and/or lot number of the limited use device 120, and the identification logic 221 may compare the acquired manufacturing date and/or lot number with the manufacturing date range and or lot number range stored in the update identification data base 225. As a result of the comparison, the identification logic 221 may allow use of the system 100 under a specially defined set of operating parameters or disable use of the system 100.

The system control logic 223 may be configured to control one or more operations of the system 100 in accordance one or more operating features as may be enabled by the identification logic 221. For example, the control logic 223 may control the operation of the energy source 114 in accordance with operating parameters defined by the set of operating features. In some instances, the enabled operating features may enable use of the pedal controller 116, and the control logic 223 may enable control the energy source 114 via the pedal controller 116.

Figure 3:
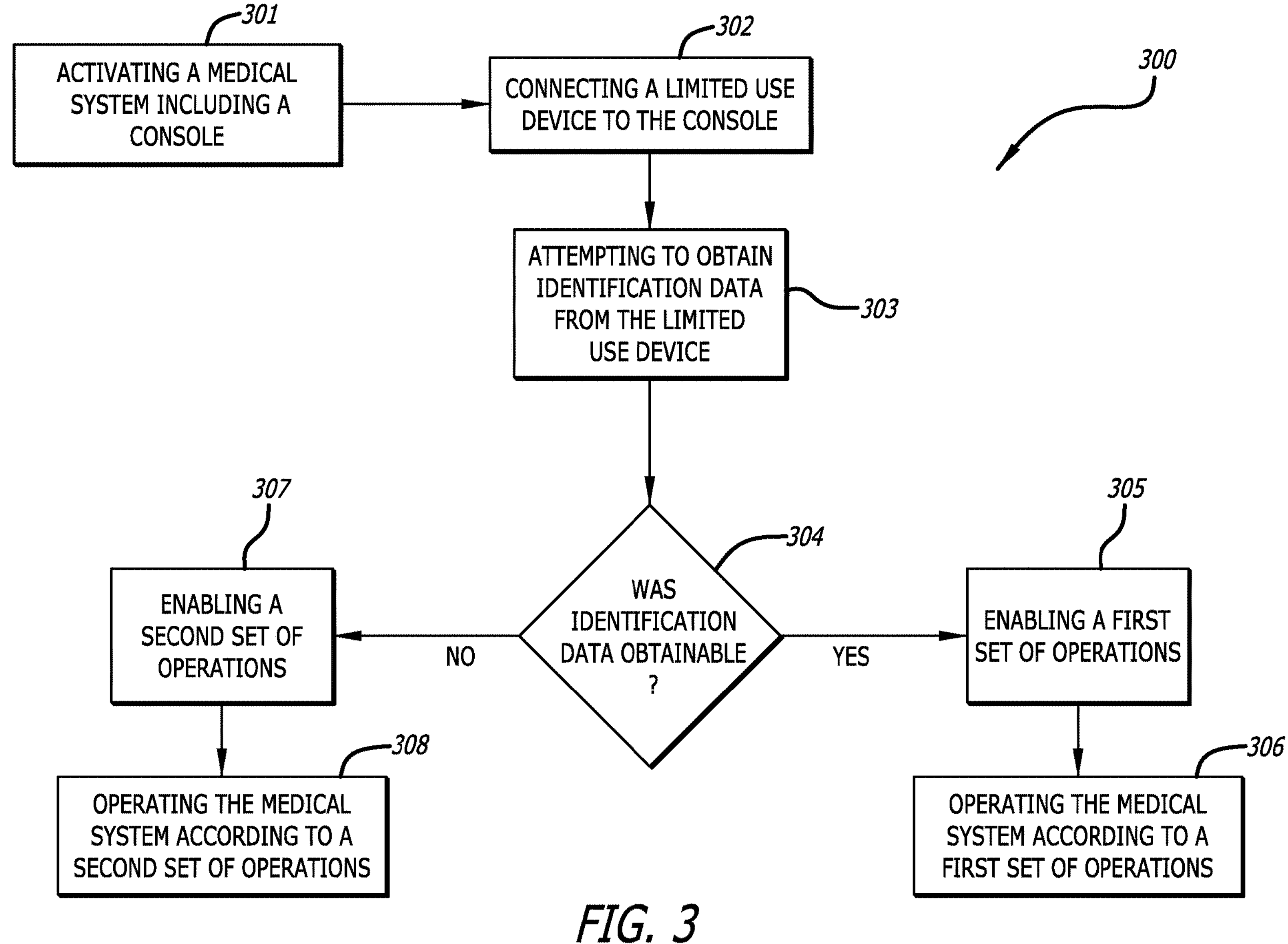
FIG. 3 is a flow chart illustrating a partially-computerized method of the system of FIG. 1, in accordance with some embodiments.

FIG. 3 illustrates an exemplary partially-computerized method 300 of the system 100, in accordance with some embodiments. The first step (block 301) represents the clinician activating the medical system and the second step (block 302) connecting a limited use device to the equipment module 110. The third step (block 303) represents the identification interface 140 attempting to obtain identification information from the limited use device 120. In the instance where the limited use device 120 includes obtainable identification information, the identification interface 140 provides identification information to the identification logic 221. In the instance, where the limited use device 120 does not include obtainable identification information, the identification interface 140 provides a signal to the identification logic 221 that the identification information is not obtainable. The fourth step (block 304) represents the identification logic 221 determining if the identification information was obtainable (YES) or unobtainable (NO). If the identification information was obtainable, then the identification logic 221 enables a first set of operations (block 305). In which instance, the clinician operates the medical system 100 according to the first set of operations (block 306). If the identification information was unobtainable, then the identification logic 221 enables a second set of operations (block 307). In which instance, the clinician operates the medical system 100 according to the second set of operations (block 308). As described above, the second set of operations may differ from the first set of operations in several ways, including ranges of therapy, ranges of equipment operation, and optional feature related operations.

Without further elaboration, it is believed that one skilled in the art can use the preceding description to utilize the invention to its fullest extent. The claims and embodiments disclosed herein are to be construed as merely illustrative and exemplary, and not a limitation of the scope of the present disclosure in any way. It will be apparent to those having ordinary skill in the art, with the aid of the present disclosure, that changes may be made to the details of the above-described embodiments without departing from the underlying principles of the disclosure herein. In other words, various modifications and improvements of the embodiments specifically disclosed in the description above are within the scope of the appended claims. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified. The scope of the invention is therefore defined by the following claims and their equivalents.

What is claimed is:

1. A medical system, comprising:

an equipment module comprising an identification interface configured to obtain identification data from a limited use device, wherein the equipment module is configured to modify operation of the medical system in accordance with a result of obtaining the identification data; and a functional interface configured to:

operatively couple the limited use device with the equipment module, and transmit energy between the equipment module and the limited use device, the energy including electrical energy and one or more of fluid, mechanical, or optical energy, wherein the functional interface:

includes a commercially-available cable connector coupled with the limited use device, the cable connector configured to couple with a corresponding equipment connector of the equipment module, and does not include a cable connector coupled with the limited use device that includes proprietary specifications or features.

2. The medical system of claim 1, wherein the medical system is configured to provide a medical treatment to a patient.

3. The medical system of claim 2, wherein the limited use device is configured to operatively engage the patient.

4. The medical system of claim 2, wherein the limited use device is configured to contact the patient.

5. The medical system of claim 1, wherein the functional interface is at least partially defined by one or more industry standards.

6. The medical system of claim 1, wherein the functional interface is non-proprietary.

7. The medical system of claim 1, wherein the identification interface is configured to wirelessly receive an identity signal from the limited use device, the identity signal including the identification data.

8. The medical system of claim 1, wherein the identification interface is coupled to a console of the equipment module, the console comprising:

a processor; and memory including identification logic stored thereon, wherein the identification logic, when executed by the processor, is configured to modify an operation of the medical system in accordance with the result of obtaining the identification data.

9. The medical system of claim 8, wherein the identification logic is configured to modify one or more treatment parameters of the medical system in accordance with the result of obtaining the identification data.

10. The medical system of claim 8, wherein the identification logic is configured to selectively enable and/or disable one or more operating features of the medical system in accordance with the result of obtaining the identification data.

11. The medical system of claim 8, wherein:

the identification data comprises a set of identification parameters, the memory comprises a corresponding set of identification parameters, an operation of the identification logic comprises comparing an identification parameter of the identification data with a corresponding identification parameter stored in memory, and the identification logic is configured to modify the operation of the medical system in accordance with a result of the comparison.

12. The medical system of claim 11, wherein the identification logic is configured to disable one or more operating features if the result of the comparison indicates that at least one identification parameter in the identification data is inconsistent with the corresponding identification parameter stored in memory.

13. The medical system of claim 12, wherein the identification logic is configured to allow operation of the medical system according to a minimal set of operating features if the result of the comparison indicates that the at least one identification parameter is inconsistent with the corresponding identification parameter.

14. The medical system of claim 11, wherein the set of identification parameters includes at least a brand of the limited use device.

15. A non-transitory, computer-readable medium having stored thereon logic, that when executed by one or more processors, causes performance of operations including:

detecting coupling of a medical device to an equipment module having a console via a functional interface configured to transmit energy between the equipment module and a limited use device, the energy including electrical energy and one or more of fluid energy, mechanical energy, or optical energy, wherein the medical device;

includes a commercially-available connector configured to couple with a corresponding equipment connector of the equipment module, and does not include a proprietary connector configured to couple with the equipment module, the proprietary connector including proprietary specifications or features; and attempting to obtain identification data of the medical device;

when the identification data is obtained and the medical device is identified, enabling the console to provide a first set of operations based on the identification data; and when the identification data is unable to be obtained, enabling the console to provide a second set of operations.

16. The non-transitory, computer-readable medium of claim 15, wherein the second set of operations is a subset of the first set of operations.

17. The non-transitory, computer-readable medium of claim 15, wherein:

the console and the medical device are components of a medical system configured to provide a therapy to a patient, and the second set of operations includes a minimal set of operations for using the medical system to provide the therapy via the medical device.

18. The non-transitory, computer-readable medium of claim 17, wherein:

the first set of operations includes a first therapy range, the second set of operations includes a second therapy range, and the second therapy range is less than the first therapy range.

19. The non-transitory, computer-readable medium of claim 17, wherein:

the medical system includes a laser for performing a laser therapy via a laser beam projected from the medical device, the first set of operations includes a first operating range of the laser, the second set of operations includes a second operating range of the laser, and the second operating range is less than the first operating range.

20. The non-transitory, computer-readable medium of claim 17, wherein:

the medical system includes one or more optional operations, the first set of operations includes at least one optional operation, and the second set of operations does not include at least one optional operation of the first set of operations.

* * * * *